United States Patent [19]

Kaspar et al.

[11] Patent Number: 4,568,517

[45] Date of Patent: Feb. 4, 1986

[54] DISINFECTION OF CONTACT LENSES

[75] Inventors: Hans H. Kaspar, Saratoga; Murray J. Sibley, Berkeley; Gordon H. Yung, Santa Clara, all of Calif.

[73] Assignee: Barnes-Hind, Inc., Sunnyvale, Calif.

[21] Appl. No.: 673,689

[22] Filed: Nov. 21, 1984

Related U.S. Application Data

[63] Continuation-in-part of Ser. No. 526,568, Aug. 25, 1983, abandoned.

[51] Int. Cl.$^4$ .............................................. A61L 21/18
[52] U.S. Cl. ...................................... 422/30; 134/143; 206/5.1; 422/301; 252/188.2; 252/188.21; 424/31
[58] Field of Search .................... 134/26–29, 134/32, 42, 143, 149, 162; 206/5.1; 422/28, 30, 292, 293, 301; 252/188.2, 188.21, 188.28; 424/19–22, 31, 35

[56] References Cited

U.S. PATENT DOCUMENTS

| | | | |
|---|---|---|---|
| 3,538,214 | 11/1970 | Polli et al. | 424/19 |
| 3,623,492 | 11/1971 | Frantz et al. | 134/143 |
| 3,829,329 | 8/1974 | O'Driscoll et al. | 134/26 |
| 3,908,680 | 9/1975 | Krezanoski | 134/42 |
| 3,912,451 | 10/1975 | Gaglia | 134/42 |
| 4,013,410 | 3/1977 | Thomas et al. | 422/30 |
| 4,179,497 | 12/1979 | Cohen et al. | 424/22 |
| 4,429,786 | 2/1984 | Hucal | 206/5.1 |

FOREIGN PATENT DOCUMENTS

| | | |
|---|---|---|
| 0082798 | 6/1983 | European Pat. Off. |
| 2309240 | 12/1976 | France |
| 1464333 | 2/1977 | United Kingdom |

OTHER PUBLICATIONS

Gasset, A. R., et al., "Hydrogen Peroxide Sterilization of Hydrophilic Contact Lenses", Arch. Ophthalmol., vol. 93, pp. 412–415 (Jun. 1975).

*Primary Examiner*—Ivars Cintins

[57] ABSTRACT

A contact lens is disinfected in an aqueous $H_2O_2$ solution. The $H_2O_2$ solution is neutralized and transformed in situ into a buffered, saline storage solution by adding a neutralizer such as sodium sulfite or sodium thiosulfate, and optional buffering agents. The neutralizer has a coating which dissolves to release the ingredients only a period of time after it is added, so that it can be put into the $H_2O_2$ solution at the same time that the lens is.

35 Claims, No Drawings

DISINFECTION OF CONTACT LENSES

This application is a continuation-in-part of our previous application Ser. No. 526,568, filed Aug. 25, 1983, now abandoned.

BACKGROUND OF THE INVENTION

This application relates to the disinfection of contact lenses, and more particularly to disinfection by waterborne chemical agents without the application of heat.

Contact lenses accumulate dirt, proteinaceous matter, and microorganisms, all of which can adversely affect the health of the eye if allowed to accumulate on the lens. Therefore, the lenses must be cleaned and disinfected regularly and preferably daily.

It is generally known that hydrogen peroxide, in aqueous solution at a concentration of 3 wt. %, can be used to disinfect contact lenses and simultaneously remove unwanted dirt and proteinaceous matter. However, the hydrogen peroxide (hereafter, $H_2O_2$) will irritate the eye if even a small residual amount remains on the lens when it is re-inserted into the eye. This problem is especially notable with soft contact lenses, which are made from a water-permeable polymer into which the $H_2O_2$ can penetrate. Removing the $H_2O_2$ from such material is particularly difficult, and has required extensive washing and soaking with saline solution. Thus, it is desirable to be able to employ $H_2O_2$ in disinfecting contact lenses, while avoiding the irritancy of residual $H_2O_2$.

DESCRIPTION OF THE PRIOR ART

U.S. Pat. No. 3,829,329 discloses immersing soft contact lenses in a normal saline (NaCl) aqueous solution of 3% $H_2O_2$, to shrink the lenses. The lenses were then boiled for 2 hours each in distilled water and normal saline solution. Adopting such a severe boiling regimen for the daily treatment of soft contact lenses would be inconvenient to the user and could cause the lenses to deteriorate.

U.S. Pat. No. 3,908,680 discloses a treatment regimen for plastic articles such as contact lenses, which employs two boiling, aqueous baths containing a peroxy compound such as $H_2O_2$, followed by cleansing with a nonionic detergent and rinsing with distilled water. This sequence, besides being overly cumbersome for daily application, is not sure to remove all residual $H_2O_2$.

U.S. Pat. No. 3,912,451 discloses that $H_2O_2$ in a solution used to sterilize soft contact lenses can be subsequently neutralized by contacting the solution with a metallic catalyst which decomposes the $H_2O_2$. This system is not sure to work quickly, as it relies on contact between the $H_2O_2$ and a solid metallic surface. Such a system also becomes less and less effective as the concentration of $H_2O_2$ declines; unfortunately, the $H_2O_2$ concentration at which this system loses efficiency can still be high enough to risk irritation to the eye of the user. In addition, this system requires several manual or mechanical steps to bring the metallic catalyst into contact with the $H_2O_2$ solution. One such mechanical approach is disclosed in U.S. Pat. No. 4,013,410, in which a mechanical timer rotates the container holding the solution so as to bring the solution into contact with a band of catalytic metal.

An article by A. R. Gasset et al., "Hydrogen Peroxide Sterilization of Hydrophilic Contact Lenses", in. Arch. Ophthalmol, Vol. 93 (June, 1975) pp. 412–415, discusses sterilizing soft contact lenses in 3% $H_2O_2$ solution. A solution of sodium thiosulfate was used to neutralize the residual $H_2O_2$ remaining in the lenses after sterilization. The authors found that sodium thiosulfate concentrations of 1.5% and 2.0% were unable to destroy all residual $H_2O_2$, while a 2.5% solution was effective. Adapting this technique to everyday practice still requires the user to take several steps that are not all performed at the same time. This risks the omission of the neutralization step, through haste, carelessness, or forgetfulness, and also risks miscalculation of the amount and concentration of the sodium thiosulfate solution that is to be added.

SUMMARY OF THE INVENTION

The present invention provides a convenient, safe, one-step process for disinfecting a contact lens. The process comprises:
(A) immersing the lens in a predetermined volume of an aqueous solution consisting essentially of $H_2O_2$ at a concentration of about 3 wt. % or less which is effective to disinfect the lens in a disinfection period of less than about 6 hours, and
(B) decomposing the $H_2O_2$ in said solution by adding to said solution, before said disinfection period has elapsed, a neutralizer comprising
one or more $H_2O_2$-neutralizing compounds in tablet or particulate form which react with $H_2O_2$ to form $H_2O$ and reaction products which are non-injurious to the eye, in an amount of said compounds effective to react with all the $H_2O_2$ in said solution, and thereby to form an aqueous solution containing said reaction products and having a pH of 6.5 to 8.5 and a tonicity of 200 to 450 milliosmol per kg of solution, and
a coating encasing said tablet or particles which coating dissolves gradually in said $H_2O_2$ solution so as to release said one or more $H_2O_2$-neutralizing compounds and water-soluble agents, only after said disinfection period has elapsed,
whereby said released compounds transform said $H_2O_2$ solution in situ into a buffered lens storage solution.

This process is particularly useful when the lens and the tablet are placed in the $H_2O_2$ solution 5 minutes or less apart, and more preferably within 1 minute or less or simultaneously.

The invention also comprises the coated neutralizer, and kits which include such a neutralizer.

DETAILED DESCRIPTION OF THE INVENTION

The present invention effectively disinfects hard and soft contact lenses, especially soft lenses, i.e. lenses made of a hydrophilic polymer such as poly(hydroxyethylmethacrylate). Other such materials are well known to those skilled in this art. The invention can be carried out in an apparatus which holds the lenses immersed in an aqueous solution while permitting the solution to contact all surfaces of both lenses. One such device is known as the "Hydra-Mat II", described in U.S. Pat. No. 3,623,492, the disclosure of which is hereby incorporated herein by reference. The present invention will be described with reference to that device. It includes two perforated baskets for holding a pair of contact lenses inside a container for a cleaning solution. The baskets are connected through gears to a knob on the cap of the container; twisting the knob spins the baskets in the cleaning solution.

The lens to be disinfected by the present invention is first removed from the eye and then cleaned, preferably by gentle rubbing between the fingers with a commercial lens cleaning solution for 15–20 seconds or by other appropriate methods for cleaning. This step, while not an essential part of the invention, helps loosen soil from the lens surface. The loosened soil and the cleaning solution are then rinsed off of the lens with saline solution or tap water, or can be washed off by placing the lens into the Hydra-Mat II baskets, adding saline solution to the container, and agitating the baskets by turning the top knob.

To disinfect the lens, it is immersed in an aqueous solution of $H_2O_2$. While $H_2O_2$ concentrations of 3 wt. % up to 10 wt. % are effective, the invention can also surprisingly be carried out quite effectively with $H_2O_2$ concentrations of less than about 3 wt. %, e.g. as low as 1 wt. %, preferably as low as 0.25 wt. %, and even as low as 0.1 wt. %. The lens can be immersed in the $H_2O_2$ solution by placing it in one lens-holding basket of the Hydra-Mat II device, and filling enough of the $H_2O_2$ solution into the container (after removing any other washing solutions) so that closing the cap over the container submerges the lens in the solution.

The low concentration of $H_2O_2$ that can be used in this process is noteworthy because the lens can be effectively disinfected in a reasonably short time. The low concentration also provides other advantages. One advantage in particular is that there is a reduced risk of harm to the eye from residual peroxide remaining in the lens. Another advantage is that lower peroxide concentrations cause little or no harm to the lens itself through chemical degradation of the polymeric structure. There should be a sufficient concentration of $H_2O_2$ that the lens is disinfected in a time up to about 6 hours; this corresponds to an $H_2O_2$ concentration of at least about 0.25 wt. %.

The concentration of $H_2O_2$ determines the length of time ("the disinfection period") for which the lens should be kept immersed in the $H_2O_2$ for disinfection. At $H_2O_2$ concentrations of 0.25 wt. %, the lens should be immersed in the $H_2O_2$ solution for about 6 hours to be sure of satisfactorily complete disinfection, whereas at 0.5 wt. % $H_2O_2$, the immersion time should be about 3 hours; and at 1.0 wt. % $H_2O_2$, immersion should be for about 2 hours, whereas a concentration of 3.0 wt. % $H_2O_2$ calls for immersion lasting about 5 minutes. One skilled in this art can readily determine the appropriate times for other initial concentrations of $H_2O_2$.

Another distinct and unobvious advantage of this process is the means by which the peroxide is removed from the lens. Specifically, a neutralizer is provided which is used to neutralize the $H_2O_2$ after a predetermined period of time and to transform the $H_2O_2$ solution into an essentially $H_2O_2$-free, buffered saline solution in which the lens can be safely stored. The lens can be removed immediately from the neutralized solution and reinserted into the eye, or it can be stored in the solution for a lengthy period of time, such as overnight.

In the broadest aspect of this invention, the neutralizer is placed into the $H_2O_2$ solution in which the lens is immersed at any time before the lens is completely disinfected, and the component(s) of the neutralizer are released into the $H_2O_2$ solution only after the lens has been in the solution long enough to be disinfected. In the preferred embodiment of the invention, the lens and the neutralizer are placed into the $H_2O_2$ solution at about the same time, that is, within 5 minutes of each other, preferably within one minute, and more preferably essentially simultaneously.

The present invention, in its preferred embodiment in which the neutralizer and lens are placed into the $H_2O_2$ solution at essentially the same time, is particularly advantageous because it lets the lens wearer perform all the necessary steps at one time. By placing the neutralizer and lens into the $H_2O_2$ together, the user does not need to return later to remove residual $H_2O_2$ from the lens or to discard the $H_2O_2$ solution. Thus, there is no chance of the user forgetting to carry out such a subsequent step. In addition, once the lens, neutralizer, and $H_2O_2$ are sealed into a container (such as the Hydra-Mat II) the user does not need to break sterility, i.e. he or she does not need to invade the sterilized environment of the lens-$H_2O_2$ system, and risk re-infecting the lens, to get rid of the $H_2O_2$ solution. The neutralizer destroys the $H_2O_2$ for the user, inside the sterilized environment.

The neutralizer includes one or more $H_2O_2$-neutralizing compounds that can react with $H_2O_2$ to form $H_2O$ and byproducts that do not injure the lens or the eye of the lens wearer. The most preferred neutralizer is sodium thiosulfate. Neutralizers that can be used include thiourea ($H_2NC(S)NH_2$), sodium sulfite ($Na_2SO_3$), thioglycerol ($HOCH_2CH(OH)CH_2SH$), sodium formate ($HCOONa$), ascorbic acid

isoascorbic acid (erythorbic acid)

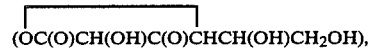

oxalic acid ($—COOH)_2$), glyoxylic acid ($OCHCOOH$), and tartaric acid ($—CHOHCOOH)_2$) Other neutralizers can work catalytically, such as platinum or other metals belonging to Period 4, 5, or 6 of the Periodic Table, or peroxidase/ catalase enzyme, but these are expensive, and do not react to form a buffered lens storage solution.

The amount of the $H_2O_2$-neutralizing compound or compounds to include in the neutralizer should be sufficient to react with all the $H_2O_2$ contained in the solution in which the lens is immersed. If sodium thiosulfate is employed, there should be at least a stoichiometric amount based on the amount of $H_2O_2$, that is, 1 mole of $Na_2S_2O_3$ per mole of $H_2O_2$. A small excess is acceptable but higher amounts of the compound(s) are not necessary. The final concentration of $H_2O_2$ in the solution after all the $H_2O_2$-neutralizing compound is dissolved and reaction has occurred should be less than 40 ppm, and is preferably less than 10 ppm. The neutralization is usually complete within 2 hours.

The neutralizer can also optionally contain water-soluble buffering agents to provide that when the neutralizer dissolves, and the $H_2O_2$ is completely neutralized, the resulting solution of buffering agents, neutralization reaction products, and excess neutralizer (if any) is a stable, buffered solution in which the lens can be safely stored.

Whether buffering agents are added or not, the resultant solution should have a pH value of 6.5 to 8.5, and more preferably 7.0 to 7.9. The tonicity of the solution should be such that the osmotic pressure of the solution will permit the immersed lens to retain its normal shape, and thus should be about 200 to about 450 milliosmolar (mOs) per kg of solution. Those familiar with this art will recognize that this range corresponds to a range of about 0.6–1.4% NaCl equivalents. The solution should be isotonic with eye fluids, or up to about 1.4% hypertonic.

Satisfactory buffering agents include a mixture of sodium borate and boric acid in amounts which permit the above pH and tonicity to be attained. Typical amounts of a sodium borate/boric acid buffer are about 0.1 to about 1.0 wt. % of the eventual solution. Other buffering systems that can be used include systems based on monobasic and dibasic sodium phosphate; sodium citrate; or sodium carbonate. It will be recognized that the amount of buffering agent is a function of the initial liquid volume of the $H_2O_2$ solution, and of the amount of neutralizing agent (because its reaction products, e.g. $Na^+$ and $SO_3^{-2}$ ions, will also influence the pH and tonicity). The amount of buffering agent can readily be determined by those skilled in this art, with reference to the parameters mentioned herein.

It should be recognized, though, that frequently the reaction between the $H_2O_2$ and the $H_2O_2$-neutralizing compound will itself form a solution whose pH and tonicity are within the indicated limits, thereby making additional buffering agents unnecessary.

The neutralizer optionally, and preferably, also contains a small amount (less than 1 wt. %) of a chelating agent such as EDTA to complex trace metals that may be present in the system. This additive helps retain the stability of the other agents in the solution, and helps any preservative that may be present retain its activity. Examples of suitable preservatives for inclusion in the tablet include potassium sorbate, sorbic acid, thimerosal, chlorhexidine, methyl and propyl parabens, chlorbutanol, benzalkonium chloride, and phenyl mercuric acetate and nitrate. These preservatives protect the neutralizer but more importantly act in solution, following dissolution of the tablet, to protect the lens. The preservative can comprise up to about 5.0 wt. % of the neutralizer.

The neutralizer can also include an acid and a base which form an effervescent couple that react in solution to generate a stream of $CO_2$ bubbles when the components dissolve. The base should preferably be sodium bicarbonate, and the acid is preferably a weak organic acid such as tartaric, citric or malic acid. The acid and base should be present in amounts which are approximately equimolar, and the acid and base together can comprise up to about 10 wt. % of the neutralizer. The $CO_2$ bubbles formed by reaction between the acid and base can aid the dispersion of any other components in the $H_2O_2$ solution, and can thereby decrease the time needed to neutralize the solution. Alternatively, the user can agitate the container of solution (as by twisting the cap of the Hydra-Mat II) after the coating around the neutralizer has dissolved, to assist the dispersion of the components.

The neutralizer (by which we include capsules and the like) has a coating which provides that the neutralizing and (if any) buffering agents will come into contact with, and dissolve into, the $H_2O_2$ solution only a predetermined length of time after the neutralizer is placed into the solution. The coating is made of material which is dissolved or decomposed gradually by $H_2O_2$; suitable materials include organically modified cellulose, such as hydroxypropylmethyl cellulose, ethyl cellulose, cellulose acetate phthalate, hydroxypropyl cellulose; polyvinyl alcohol; and dibutyl phthalate. The thickness of the coating can readily be determined as follows. The length of time ($t_c$) for which the coating must keep the other agents from dissolving is readily determined from the length of the disinfection period ($t_d$), which as discussed above is a function of the concentration of the $H_2O_2$ solution that is being used. If the lens and the neutralizer are placed into the $H_2O_2$ solution at the same time, then $t_c$ equals $t_d$. If the neutralizer is to be added a higher number of minutes after the lens is placed into the $H_2O_2$ solution, then $t_c$ is less than $t_d$ by that number; if the neutralizer is to be added a higher number of minutes before the lens is immersed, then $t_c$ exceeds $t_d$ by that number. One can independently determine the rate at which a given coating material is dissolved by a solution of $H_2O_2$ at the concentration being used, and by multiplying $t_c$ by the rate of the $H_2O_2$ concentration being used, one can calculate how much of that coating to apply to a neutralizer for use with an $H_2O_2$ solution having that concentration. It is advantageous to make the coating 5 to 15% thicker than the calculated value, to ensure that the lens is exposed to unneutralized $H_2O_2$ for a sufficient disinfection time and to compensate for any slight loss of $H_2O_2$ due to reaction with the coating material.

The neutralizer can be a coated tablet, which can be made by dry blending the neutralizing and buffering agents, as well as the optional preservative and chelating agent, to obtain a uniform mixture, and then tabletting the blend employing conventional tabletting machinery. Separately, an amount of the coating material sufficient to form coatings of the desired thickness is dissolved in a solvent such as ethanol or acetone, and the solution is sprayed onto the tablets so as to form a uniform coating. The solvent is then evaporated, leaving the desired coating.

Alternatively, and preferably, instead of having all desired ingredients in one coated tablet one can prepare a number of particles each of which has a coating with the characteristics described above, provided that the particles provide in the aggregate a sufficient amount of the $H_2O_2$-neutralizing compound(s) and of the other components to achieve the neutralization and (optional) buffering and effervescing functions described herein. Each particle can be homogeneous, that is, contains only one compound, or the particles can be heterogeneous, that is, they may contain two or more of the desired compounds. For instance, if an effervescent couple is used, it may be advantageous to put the acid and the base into separate coated particles. The particles can be formed and coated in the manner described above for tablets. The particles can be sold and used conveniently in the form of foil packets, two-piece capsules, or the like, each of which contains enough of the $H_2O_2$-neutralizing compound(s) and the other desired ingredients to comprise one "dose". It will be appreciated that any number of particles, e.g. 2 to 100 or more, can be used. After the user washes the lens and places it into the $H_2O_2$ solution, the user simply opens the packet, capsule, or other container and dumps all the contents into the $H_2O_2$ solution, instead of dropping a tablet into the solution in the manner described below.

It will be recognized that all components of the tablet should be non-irritating to the eye when in solution. Standard tests for determining non-irritability to the eye are known to those skilled in this field. The $H_2O_2$ solutions can contain up to 0.05 wt. % of a stabilizer, and if so it should not react with or discolor the lens. A satisfactory stabilizer is a mixture of sodium stannate and sodium pyrophosphate, in a ratio of about 60:40 to 40:60 by weight.

The invention is described in the following Examples:

EXAMPLES 1-6

Mixtures of materials were compounded into preparations having the composition given below. Each preparation was added to 7 ml of an aqueous solution of 0.5 wt. % $H_2O_2$. The time required for neutralization, and the pH and tonicity of the final solution, are also given. In each case, the final concentration of $H_2O_2$ was less than 40 ppm. Examples 2 and 6 were effervescent, i.e. on dissolution bubbles of $CO_2$ formed which dispersed the other components throughout the solution.

| Ingredients (mg): | Example No.: | | | | | |
|---|---|---|---|---|---|---|
|  | 1 | 2 | 3 | 4 | 5 | 6 |
| Sodium thiosulfate | 190 | 180 | 180 | 180 | 180 | 190 |
| Potassium sorbate | 10 | — | — | 10 | 10 | 10 |
| Disodium EDTA | 10 | 2 | — | 2 | 2 | 10 |
| Boric acid | 42 | — | 7.5 | 7.5 | 15 | 42 |
| Sodium bicarbonate | — | 12 | 5 | 5 | 10 | 12 |
| Citric acid | — | 8 | — | — | — | 8 |
| Sodium phosphate (monobasic) | — | — | 7 | 7 | — | — |
| Sodium phosphate (dibasic) | — | — | 10 | 10 | — | — |
| Time (hr) to complete neutralization | 1-2 | 4 | 4 | 4 | 3 | 1-2 |
| pH of neutralized solution | 7.9 | 7.3 | 7.2 | 7.0 | 7.9 | 7.9 |
| Tonicity (mOs/kg) of neutralized solution | 410. | 275. | 303. | 319. | 316. | 410. |

Another embodiment of this invention comprises a kit for disinfecting lenses with an $H_2O_2$ solution and for neutralizing the $H_2O_2$ solution. The kit comprises means for washing the lens, and a tablet or particulate neutralizer of the type described herein. The lens washer means is advantageously of the type having a container open at its top for receiving lens washing fluid and a lens case agitator;

a lidlike member removably mounted on the top end of the container and open at both ends and having a transverse partition intermediate its ends; said partition having an aperture extending therethrough;

a lens case agitator pivotally mounted in said aperture in the partition and extending into said container and having depending lens case supporting means and an upper end extending above the partition and having a spur gear thereon;

a knoblike member pivotally received in the upper end of the lidlike member and having finger grasp means for rotating the same and internal gear teeth therein;

planetary gear means pivotally mounted on said transverse top portion of the lidlike member and interposed between said spur gear on the agitator and said internal gear teeth in the knoblike member for imparting rotation to said agitator member whereby a lens carried in said lens case is washed in the liquid in the container;

and a lens case, attached to the lens case agitator, for holding a lens in communication with liquid in said container (a small concave bowl, having perforations to let liquid pass through but not letting the lens fall therethrough, and having a detachable lid, is satisfactory);

or equivalents of such a device.

The kit is employed in the manner described herein, to clean and disinfect a contact lens. The composition of the tablet or the quantity of particulate neutralizer is predetermined to be used with a specified volume of aqueous $H_2O_2$ solution having a specified concentration, and instructions are provided with the kit to inform the user of the strength and volume of the $H_2O_2$ solution to use. More advantageously, the kit includes a bottle of an aqueous solution of $H_2O_2$, whose concentration is predetermined (0.25-3 wt. %) in conjunction with the composition of the tablet. In this embodiment, the only measurement required of the user is pouring a specified amount of the solution into the container of the lens washer. The amount can be marked by a line provided on the container at the height which corresponds to the specified volume. The user is simply instructed to pour solution from the bottle to this line, to place the lenses into the lens case (or each lens into its own lens case, to avoid confusing the left lens with the right lens), at the same time placing a tablet (or adding the contents of one package of neutralizer, as the case may be) into the container, and to close the lid of the container.

The user can be instructed to wait a predetermined period of time, by the end of which the lenses are sure to be cleaned and the $H_2O_2$ to be neutralized. In general, if the coating has dissolved it will impart a slight turbidity to the solution; one can use the presence of this turbidity as a guide to whether the neutralization has occurred.

What is claimed is:

1. A process for disinfecting a contact lens, comprising (A) immersing the lens in a predetermined volume of an aqueous disinfecting solution consisting essentially of $H_2O_2$ at a concentration of about 3 wt. % or less which is effective to disinfect the lens in a disinfection period of less than about 6 hours, and (B) decomposing the $H_2O_2$ in said disinfecting solution by adding to said solution, before said disinfection period has elapsed, a neutralizer in the form of a tablet or a plurality of particles and comprising one or more $H_2O_2$-neutralizing compounds which react with $H_2O_2$ to form $H_2O$ and reaction products which are non-injurious to the eye, in an amount of said one or more compounds effective to react with all the $H_2O_2$ in said solution, and thereby to form an $H_2O_2$ solution containing said reaction products and having a pH of 6.5 to 8.5 and a tonicity of 200 to 450 milliosmol per kg of solution, and a coating encasing said tablet or each of said particles which coating dissolves gradually in said $H_2O_2$ solution, so as to release said one or more $H_2O_2$-neutralizing compounds only after said disinfection period has elapsed, whereby said released neutralizing compounds transform said $H_2O_2$ solution in situ into a buffered, saline lens storage solution.

2. The process of claim 1 wherein said disinfection period is less than about 3 hours.

3. The process of claim 1 wherein the concentration of $H_2O_2$ is about 1 wt. % or less.

4. The process of claim 1 wherein said coating is selected from the group consisting of organically modified cellulose, polyvinyl alcohol, and dibutyl phthalate.

5. The process of claim 1 wherein said lens and said neutralizer are placed into said $H_2O_2$ solution within 5 minutes of each other.

6. The process of claim 1 wherein said lens and said neutralizer are placed into said $H_2O_2$ solution within 1 minute of each other or simultaneously.

7. The process of claim 1 wherein the said neutralizer also contains up to about 10 wt. % of a mixture of an acid and a base which react in solution to form $CO_2$ gas.

8. The process of claim 1 wherein the concentration of $H_2O_2$ in said buffered, saline lens storage solution is less than about 40 ppm.

9. The process of claim 1 wherein said neutralizer also contains up to about 1 wt. % of a chelating agent and up to about 5 wt. % of a preservative.

10. The process of claim 1 wherein said one or more $H_2O_2$-neutralizing compounds comprises sodium thiosulfate or sodium sulfite.

11. The process of claim 1 wherein the lens is not removed from said aqueous solution until after the solution has been transformed into a buffered, saline lens storage solution.

12. The process of claim 11 wherein the lens and the tablet are sealed together into a closed container containing said disinfecting solution, and the container is not opened again until after said disinfecting solution has been transformed into a buffered, saline lens storage solution.

13. A process for disinfecting a contact lens, comprising (A) immersing the lens in a predetermined volume of an aqueous disinfecting solution consisting essentially of $H_2O_2$ at a concentration of about 3 wt. % or less which is effective to disinfect the lens in a disinfection period of less than about 6 hours, and (B) decomposing the $H_2O_2$ in said disinfecting solution by adding to said solution, before said disinfection period has elapsed, a neutralizer in the form of a tablet or a plurality of particles and comprising one or more $H_2O_2$-neutralizing compounds which react with $H_2O_2$ to form $H_2O$ and reaction products which are non-injurious to the eye, in an amount of said one or more compounds effective to react with all the $H_2O_2$ in said solution;

one or more water-soluble agents in an amount thereof effective to provide that an aqueous solution having said predetermined volume and containing said reaction products and said water-soluble agents has a pH of 6.5 to 8.5 and a tonicity of 200 to 450 milliosmol per kg of solution, and a coating encasing said tablet or each of said particles which coating dissolves gradually in said $H_2O_2$ solution, so as to release said one or more $H_2O_2$-neutralizing compounds and water-soluble agents only after said disinfection period has elapsed, whereby said released neutralizing compounds and agents transform said $H_2O_2$ solution in situ into a buffered, saline lens storage solution.

14. The process of claim 13 wherein said water-soluble agents comprise a mixture of sodium borate and boric acid.

15. The process of claim 13 wherein the amount of said water-soluble agents is effective to provide that said resulting solution has a pH of about 7.0 to about 7.9.

16. The process of claim 13 wherein said coating is selected from the group consisting of organically modified cellulose, polyvinyl alcohol, and dibutyl phthalate.

17. The process of claim 13 wherein said neutralizer also contains up to about 1 wt. % of a chelating agent and up to about 5 wt. % of a preservative.

18. The process of claim 13 wherein the neutralizer also contains up to 10 wt. % of a mixture of an acid and a base which react in solution to form $CO_2$ gas.

19. The process of claim 13 wherein said lens and said neutralizer are placed into said $H_2O_2$ solution within 5 minutes of each other.

20. The process of claim 13 wherein said lens and said neutralizer are placed into said $H_2O_2$ solution within 1 minute of each other or simultaneously.

21. A kit for disinfecting a contact lens in a predetermined volume of an aqueous disinfecting solution of $H_2O_2$ having a predetermined concentration, and for neutralizing the $H_2O_2$ in said solution after a disinfection period which is a function of said predetermined concentration and for transforming the solution in situ into a buffered isotonic lens storage solution; said kit comprising means for washing the lens, and a neutralizer in the form of a tablet or a plurality of particles, wherein said neutralizer comprises one or more $H_2O_2$-neutralizing compounds which react with $H_2O_2$ to form $H_2O$ and reaction products which are non-injurious to the eye, in an amount of said one or more compounds effective to react with all the $H_2O_2$ in said disinfecting solution and thereby to form an aqueous solution containing dissolved therein said reaction products and having a pH of 6.5 to 8.5 and a tonicity of 200 to 400 milliosmol per kg of solution, and a coating encasing said tablet or each of said particles, which coating is characterized in that when said coated tablet or particles is placed in said $H_2O_2$ solution before the end of said disinfection period, said coating gradually dissolves in the $H_2O_2$ solution, and releases said one or more neutralizing compounds only after said disinfection period has elapsed.

22. The kit according to claim 21, which further comprises up to 10 wt. % of an acid and a base which react in solution to form $CO_2$ gas and water-soluble products which are non-injurious to the eye.

23. The kit of claim 22 wherein said acid is selected from the group consisting of citric, tartaric, and malic acids, and said base is sodium bicarbonate.

24. The kit of claim 21 wherein said means for washing the lens comprises a container open at its top for receiving said predetermined volume of said $H_2O_2$ solution and a lens case agitator;

a lidlike member removably mounted on the top end of the container and open at both ends and having a transverse partition intermediate its ends;

said partition having an aperture extending therethrough;

a lens case agitator pivotally mounted in said aperture in the partition and extending into said container and having depending lens case supporting means and an upper end extending above the partition and having a spur gear thereon;

a knoblike member pivotally received in the upper end of the lidlike member and having finger grasp means for rotating the same and internal gear teeth therein;

planetary gear means pivotally mounted on said transverse top portion of the lidlike member and interposed between said spur gear on the agitator and said internal gear teeth in the knoblike member for imparting rotation to said agitator member whereby a lens carried in said lens case is washed in the liquid in the container; and lens case means, attached to said lens case supporting means, for holding a lens in communication with said solution.

25. The kit of claim 21 wherein said coating is characterized in that when the neutralizer is placed in said $H_2O_2$ solution up to 5 minutes after the beginning of said disinfection period, said coating dissolves only after said disinfection period has elapsed.

26. The kit of claim 21 further comprising a bottle of an aqueous solution of $H_2O_2$ having said predetermined concentration.

27. A kit for disinfecting a contact lens in a predetermined volume of an aqueous disinfecting solution of $H_2O_2$ having a predetermined concentration, and for neutralizing the $H_2O_2$ in said solution after a disinfection period which is a function of said predetermined concentration and for transforming the solution in situ into a buffered isotonic lens storage solution; said kit comprising means for washing the lens, and a neutralizer in the form of a tablet or a plurality of particles, wherein said neutralizer comprises one or more $H_2O_2$-neutralizing compounds which react with $H_2O_2$ to form $H_2O$ and reaction products which are non-injurious to the eye, in an amount of said one or more compounds effective to react with all the $H_2O_2$ in said disinfecting solution, one or more water-soluble agents in an amount thereof effective to provide that an aqueous solution having said predetermined volume and containing dissolved therein said reaction products and said water-soluble agents has a pH of 6.5 to 8.5 and a tonicity of 200 to 400 milliosmol per kg of solution, and a coating encasing said tablet or each of said particles, which coating is characterized in that when said coated tablet or particles is placed in said $H_2O_2$ solution before the end of said disinfection period, said coating gradually dissolves in the $H_2O_2$ solution, and releases said one or more neutralizing compounds and water-soluble agents only after said disinfection period has elapsed.

28. The kit according to claim 27 wherein said one or more water-soluble agents are selected from the group consisting of boric acid, sodium borate, and mixtures thereof.

29. The kit of claim 27 further comprising a bottle of an aqueous solution of $H_2O_2$ having said predetermined concentration. .

30. A neutralizer suitable for use in a kit for disinfecting a contact lens in a predetermined volume of an aqueous disinfecting solution of $H_2O_2$ having a predetermined concentration, and for neutralizing the $H_2O_2$ in said solution after a disinfection period which is a function of said predetermined concentration and for transforming the solution in situ into a buffered isotonic lens storage solution, which kit comprises means for washing the lens, and a neutralizer; which neutralizer is in the form of a tablet or a plurality of particles and comprises one or more $H_2O_2$-neutralizing compounds which react with $H_2O_2$ to form $H_2O$ and reaction products which are non-injurious to the eye, in an amount of said one or more compounds effective to react with all the $H_2O_2$ in said disinfecting solution and thereby to form an aqueous solution containing dissolved therein said reaction products and having a pH of 6.5 to 8.5 and a tonicity of 200 to 400 milliosmol per kg of solution, and a coating encasing said tablet or each of said particles which coating is characterized in that when said coated tablet or particles is placed in said $H_2O_2$ solution before the end of said disinfection period, said coating gradually dissolves in the $H_2O_2$ solution, and releases said one or more neutralizing compounds only after said disinfection period has elapsed.

31. The neutralizer according to claim 30, which further comprises up to 10 wt. % of an acid and a base which react in solution to form $CO_2$ gas and water-soluble products which are non-injurious to the eye.

32. The neutralizer of claim 31 wherein said acid is selected from the group consisting of citric, tartaric, and malic acids, and said base is sodium bicarbonate.

33. The neutralizer of claim 30 wherein said coating is characterized in that when the neutralizer is placed in said $H_2O_2$ solution up to 5 minutes after the beginning of said disinfection period, said coating dissolves only after said disinfection period has elapsed.

34. A neutralizer suitable for use in a kit for disinfecting a contact lens, in a predetermined volume of an aqueous disinfecting solution of $H_2O_2$ having a predetermined concentration, and for neutralizing the $H_2O_2$ in said solution after a disinfection period which is a function of said predetermined concentration and for transforming the solution in situ into a buffered isotonic lens storage solution, which kit comprises means for washing the lens, and a neutralizer; which neutralizer is in the form of a tablet or a plurality of particles and comprises one or more $H_2O_2$-neutralizing compounds which react with $H_2O_2$ to form $H_2O$ and reaction products which are non-injurious to the eye, in an amount of said one or more compounds effective to react with all the $H_2O_2$ in said disinfecting solution, one or more water-soluble agents in an amount thereof effective to provide that an aqueous solution having said predetermined volume and containing dissolved therein said reaction products and said water-soluble agents has a pH of 6.5 to 8.5 and a tonicity of 200 to 400 milliosmol per kg of solution, and a coating encasing said tablet or each of said particles which coating is characterized in that when said coated tablet or particles is placed in said $H_2O_2$ solution before the end of said disinfection period, said coating gradually dissolves in the $H_2O_2$ solution, and releases said one or more neutralizing compounds and water-soluble agents only after said disinfection period has elapsed.

35. The neutralizer according to claim 34 wherein said one or more water-soluble agents are selected from the group consisting of boric acid sodium borate, and mixtures thereof.

* * * * *